United States Patent [19]

Barton

[11] 4,072,894
[45] Feb. 7, 1978

[54] ROTATING PIPELINE INSPECTION APPARATUS
[75] Inventor: Robert D. Barton, Houston, Tex.
[73] Assignee: AMF Incorporated, White Plains, N.Y.
[21] Appl. No.: 615,003
[22] Filed: Sept. 19, 1975

Related U.S. Application Data
[63] Continuation of Ser. No. 299,009, Oct. 19, 1972, abandoned, which is a continuation of Ser. No. 56,491, July 20, 1972, abandoned.

[51] Int. Cl.² ............................................. G01R 33/12
[52] U.S. Cl. ........................................ 324/221; 324/240
[58] Field of Search ................................ 324/37, 40; 15/104.06 R

[56] References Cited
U.S. PATENT DOCUMENTS 2,315,133  3/1943  Riney et al. .................. 15/104.06 R
2,940,302  6/1960  Scherbatskoy .................... 324/34 R
3,328,681  6/1967  Wood ................................ 324/37
3,449,662  6/1969  Wood ................................ 324/37

FOREIGN PATENT DOCUMENTS
631,988  11/1949  United Kingdom .................. 324/37

Primary Examiner—Robert J. Corcoran
Attorney, Agent, or Firm—George W. Price; Charles J. Worth

[57] ABSTRACT

Inspection apparatus adapted to be propelled through a pipeline. Means are provided to establish a circumferentially directed flux field in wall of pipe, and longitudinally extending flexible fins or flaps of elastomeric material curve outwardly from apparatus to resiliently hold flux leakage detection means against wall of pipe. Means responsive to axial movement of apparatus imparts helical movement of apparatus. Apparatus is readily adapted to inspect pipelines of different sizes.

12 Claims, 5 Drawing Figures

INVENTOR
ROBERT D. BARTON
BY John H. Gallagher
ATTORNEY

INVENTOR
ROBERT D. BARTON
BY
John H. Gallagher
ATTORNEY

ROTATING PIPELINE INSPECTION APPARATUS

This application is a continuation of application Ser. No. 299,009 filed Oct. 19, 1972, entitled Rotating Pipeline Inspection Apparatus by R. D. Barton, now abandoned, which application is a continuation of application Ser. No. 56,491, filed July 20, 1970 by R. D. Barton, entitled Rotating Pipeline Inspection Apparatus, now abandoned.

BACKGROUND OF THE INVENTION

Buried pipelines that transport fluid products such as natural gas, crude oil, and other petroleum products are subject to damage due to physical forces applied to them, and due to chemical and electrolytic action. To assure that a pipeline is safe for continued operation it is periodically inspected for flaws by nondestructive testing apparatus which is carried through the interior of the pipeline by means of a pig. The pig is propelled through the pipeline by the fluid being transported therethrough.

One of the more serious flaws that potentially may make the pipeline unsafe for continued operation is a longitudinally extending anomaly in the wall of the pipe. Apparatus for detecting longitudinally extending flaws in a buried pipeline are disclosed in U.S. Pat. Nos. 3,238,448 by Wood et al., and 3,483,466 by Crouch et al.

Although the devices disclosed in those patents are useful, the device shown in U.S. Pat. No. 3,238,448 requires that a power source carried on the apparatus rotate a portion of the apparatus that carried the flaw detection means. Also, slip rings are required to couple detected flaw signals and electrical power to and from other portions of the apparatus. These requirements add complexity to the design and maintenance of the apparatus. Satisfactory operation of slip rings in a pipeline environment is particularly troublesome. In order to minimize the complexities mentioned above, the device of U.S. Pat. No. 3,483,466 was constructed in such a manner that longitudinally extending anomalies could be detected without the need for mechanically rotating a portion of the apparatus. This simplified the device and eliminated the need for the additional power source and slip rings associated with the rotating portion. However, because optimum sensitivity of detection of longitudinally extending anomalies is achieved when the flux leakage detector passes transversely across the longitudinally extending anomaly, the device of U.S. Pat. No. 3,483,466 does not provide optimum sensitivity of detection.

Additionally, in the prior devices discussed above, the search shoes which house the flaw detecting elements, such as search coils, are supported by mechanisms which involve moving and sliding parts and springs. The mechanisms are subject to corrosion and considerable wear, damage, and even loss when they encounter mashes, weld "icicles", valves, and traps, for example.

BRIEF SUMMARY OF INVENTION

The improved pipeline inspection apparatus of the invention includes means for establishing a circumferentially directed magnetic flux field in the wall of the pipe and flaw detecting means adapting to scan or wipe the interior surface of the pipe. The flaw detecting means are carried on longitudinally extending appendages of a flexible material which resiliently maintains the flaw detecting means in intimate contact with the pipe wall. Means for supporting the apparatus within the pipeline imparts a rotary motion to the entire inspection apparatus as it is propelled through the pipeline, thus causing the flaw detection means to follow a helical path through the pipeline and to pass transversely across any longitudinally extending anomaly in the pipe wall.

The inspection apparatus is constructed in such a way that it may be readily adapted for use in different pipelines respectively made of different diameter pipes.

BRIEF DESCRIPTION OF THE DRAWINGS

FIG. 5 also illustrates an alternative construction of the magnetizing and flaw detection portion of the inspection apparatus.

DETAILED DESCRIPTION OF THE INVENTION

Figure 1:
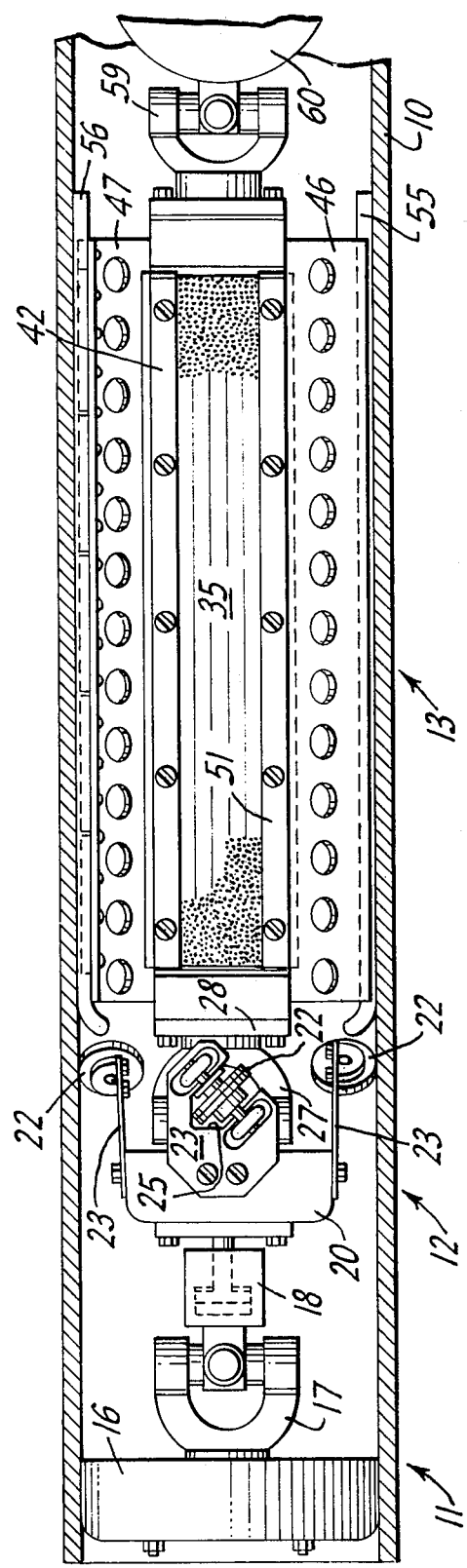
FIGS. 1 and 2 are orthogonal longitudinal views, partially in section, of the inspection apparatus of this invention.
Figure 2:
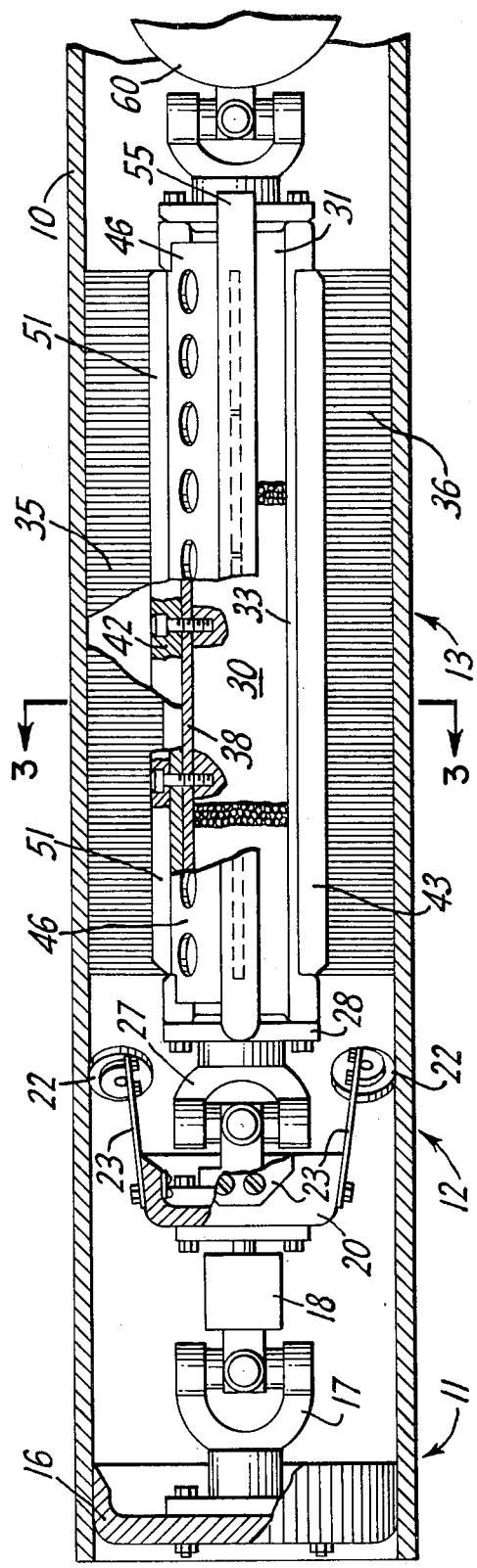

Referring to FIGS. 1 and 2, the inspection apparatus is illustrated as it would appear within a section of pipeline 10. The apparatus is comprised of three principal sections; a propelling section 11, a rotating section 12, and an inspection section 13. Propelling section 11 is comprised of one or more elastomeric cup or packer 16 which engages the entire circumference of the inside wall of the pipe and acts as a sliding seal or packer which is forced toward the left by the pressure of the fluid which is being transported through the pipeline in the direction from right to left.

A universal joint 17 and a swivel joint 18 connect cup 16 to the rotating section 12. Rotating section 12 includes an elastomeric wheel support member 20 which may be cup-shaped as illustrated. Three or more supporting wheels 22 are rotatably mounted on respective support brackets 23 which are secured in spaced relationship about the periphery of wheel support member 20. Support brackets 23 are resilient to permit wheels 22 to ride over dents and protrusions in the pipeline, yet they are stiff enough so that in cooperation with wheels 22 they tend to have a centering action to help maintain the apparatus substantially centered within the pipeline 10.

As best seen in FIG. 1, each wheel 22 is mounted within a cut-out portion 25 in its respective support bracket 23. Furthermore, all of the wheels 22 are canted or inclined in the same direction relative to the longitudinal axis of pipe 10 so that the section 12 is caused to rotate as it is drawn through pipe 10 by the propelling section 11. Because of swivel joint 18, rotating section 12 rotates independently of propelling section 11 whose forward motion is substantially without rotation.

Another universal joint 27 and a connector plate 28 connect rotating section 12 to inspection section 13 so that rotating section 12 imparts its rotary motion to inspection section 13. Universal joints 17 and 27 allow the various sections of the apparatus to bend with respect to each other to permit the apparatus to negotiate bends in the pipeline without becoming lodged therein.

Figure 3:
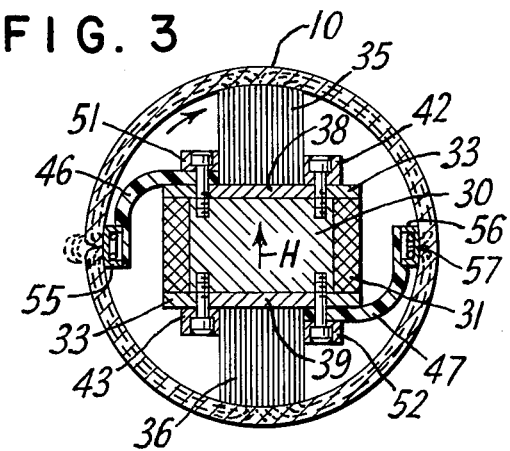
FIG. 3 is a transverse sectional view taken at sections 3—3 of FIG. 2.

FIGS. 1-3 illustrate the inspection apparatus as it is adapted to inspect the smallest diameter pipeline contemplated to be inspected by one basic piece of apparatus of this invention. The inspection section is comprised of a longitudinally extending magnetic core member 30 having a solenoid 31 wound thereabout to form an electromagnet which provides a unidirectional magnetic field H directed vertically, as viewed in FIG. 3. Longitudinally extending flange members 33 secured, as by welding, at the four corners of core member 30 form a bobbin-like construction upon which solenoid 31 is wound.

Positioned on the top and bottom surfaces of core member 30, and between a respective pair of flange members 33, are respective wire brush pole pieces 35 and 36 which are formed of magnetic flux conductive bristles. The wire brushes are mounted by any conventional means, not illustrated, to respective sole plates 38 and 39 of magnetic material. Thus, good magnetic flux conductive paths are established from core 30 to wire brushes 35 and 36. Wire brush pole pieces 35 and 36 extend longitudinally substantially the entire length of inspection section 13 and extend radially to make intimate contact with the inner surface of pipe 10 at diametrically opposed regions. The magnetic path just described establishes a circumferentially direct magnetic flux field in each half of the wall of pipe 10. Longitudinally extending cracks and flaws in the wall of pipeline 10 will interrupt the circumferentially directed flux field and will create leakage flux which may be detected by suitable means.

In FIG. 3 the right edge of magnetic sole plate 38 and the left edge of sole plate 39 are held in contact with core 30 by means of longitudinally extending retainer bars 42 and 43 which are held in place by bolts threaded into core member 30.

The opposite edges of sole plates 38 and 39 are held in contact with core 30 by the edge portions of respective longitudinally extending appendages such as fins or flaps 46 and 47, described below, and by longitudinally extending retainer bars 51 and 52 which are held in place by bolts threaded into core member 30.

Fins 46 and 47 are each made of a unitary sheet of elastomeric material such as rubber or a plastic such as polyurethane which is resilient and yet durable enough to withstand considerable wear and physical shock force. The characteristics of the elastomeric material, and the width and thickness of the sheets are chosen so that when bent as illustrated in FIG. 3, they hold the respective longitudinally extending transducer housing members 55 and 56 in firm, but yieldable, contact with the inner surface of pipe 10. As best seen in FIGS. 1 and 2, fins 46 and 47 may be perforated along their lengths to facilitate their bending. Fins 46 and 47 are bent in the appropriate direction so that transducer housings 55 and 56 are at the trailing or free edges of the fins as inspection section 13 rotates within pipe 10. As illustrated in FIG. 3, the inspection apparatus would rotate in a clockwise direction relative to pipe 10.

Disposed within and along the lengths of transducer housing members 55 and 56 are respective pluralities of flaw detection means such as magnetic flux leakage sensing coils 57 whose construction and operation are understood by those skilled in the art of magnetic non-destructive testing. Transducer housing members 55 and 56 are made of a wear resistant, nonmagnetic material such as stainless steel. The size, shape, and arrangement of flux leakage sensing coils in transducer housing members 55 and 56 are proportioned so that substantially complete flaw inspection may be achieved along the lengths of the transducer housing members. Additionally, the inclination of wheels 22, and thus the pitch of the helical path followed by inspection section 13, is proportioned relative to the lengths of transducer housing members 55 and 56 so that complete inspection coverage of the pipe wall is achieved as the inspection apparatus passes helically through the pipeline. The helical motion causes the flaw detection coils to pass transversely across a longitudinally extending anomaly in the wall of pipe 10.

The leading edges of transducer housing members 55 and 56 are bowed inwardly to permit the housing members to ride up and over protrusions on the inside surface of the pipe. It may be desirable to form the transducer housing members 55 and 56 in a plurality of adjacent segmented parts to that adjacent parts may bend and/or twist relative to each other. This type of construction will minimize any tendency of an entire housing member to lift off of the surface of the pipe when a protrusion is encountered. The yieldable nature of fin members 46 and 47 throughout their entire lengths will aid in avoiding the complete lift off of the transducer housing members from the pipe wall surface when using segmented housing members.

Inspection section 13 is connected at its right end by universal joint 59 to additional apparatus such as flaw signal circuitry and recorders for processing the flaw signals and battery packs for energizing the inspection equipment. The additional equipment is contained in a housing 60, FIGS. 1 and 2, which rotates along with the inspection section 13 as the apparatus moves through the pipeline. Housing 60 is provided with canted or inclined supporting wheels similar to the wheels 22 of FIGS. 1 and 2. It may be seen that slip rings are not required to couple the electromagnet, if used, and the flaw detection coils in inspection section 13 to the batteries and electronic and recording equipment carried in housing 60 since both parts of the apparatus rotate together.

As previously mentioned, the inspection apparatus of this invention may be readily adapted to inspect different pipelines made of different diameter pipes. FIG. 3, for example, illustrates the apparatus adapted to inspect a pipeline having one diameter, and FIGS. 4 and 5 illustrate the apparatus adapted to inspect pipelines of successively larger diameters.

Figure 4:
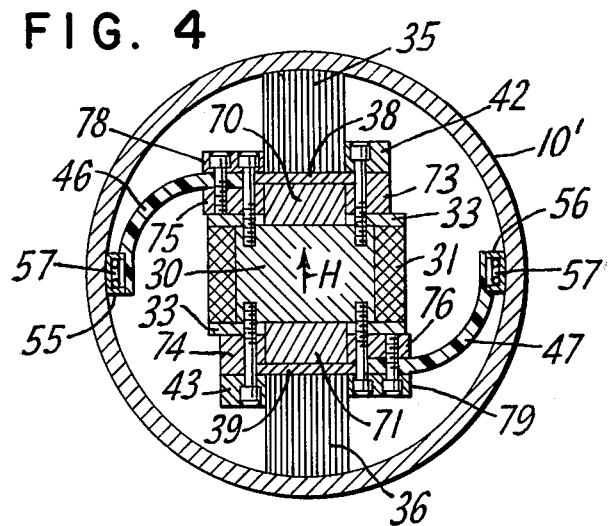
FIGS. 4 and 5 are sectional views similar to FIG. 3 showing the construction of the basic inspection apparatus adapted for use in successively larger pipes.
Figure 5:
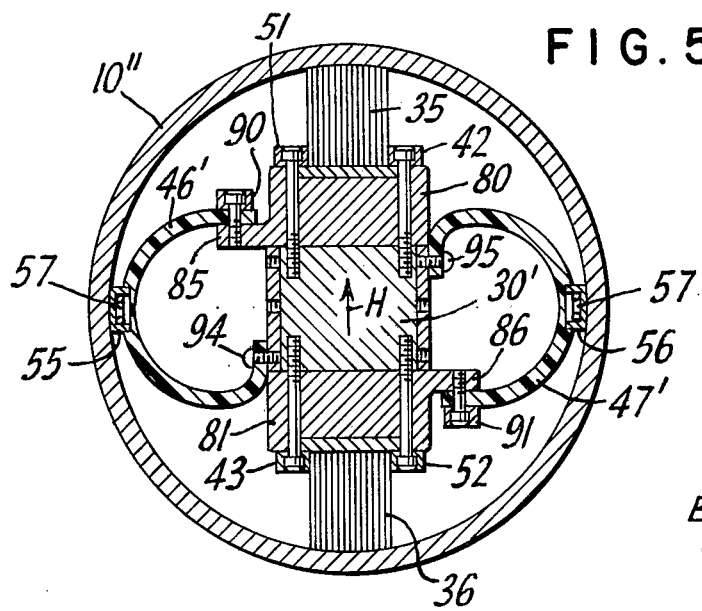

In FIG. 4, core member 30, solenoid 31, wire brush pole pieces 35 and 36, the appendages such as fin members 46 and 47, and transducer housing members 55 and 56 are the same as illustrated in FIG. 3. In order for the pole pieces 35 and 36 to make good flux-conductive contact with the wall of the larger diameter pipe 10', longitudinally extending magnetically conductive spacer bars 70 and 71 are placed between core member 30 and the sole plates 38 and 39 of the wire brush pole pieces 35 and 36. Additional longitudinally extending pieces 73 and 74 are placed under respective retainer bars 42 and 43 to secure the right and left edges, respectively, of sole plates 38 and 39.

The locations of fin members 46 and 47 also are moved radially outwardly by means of spacer bars 75 and 76. Retainer bars 78 and 79 receive bolts to secure fins 46 and 47 to spacer bars 75 and 76, and to secure those spacer bars to core member 30. It may be seen by comparing FIGS. 3 and 4 that fin member 46, for example, has been moved upwardly from core member 30 and outwardly from pole piece 35 so that transducer housing member 55 still makes firm contact with the wall of the larger diameter pipe 10'.

For inspection apparatus constructed as illustrated in FIG. 4, appropriate changes also must be made to the rotating section 12, FIGS. 1 and 2, to assure that wheels 22 maintain engagement with the inside surface of the larger diameter pipe 10'. For example, larger diameter wheels may be used, differently shaped supporting brackets 23 may be used, or a different size cup member 20 may be used. Larger diameter cup 16 also would be used in propelling section 11.

The functioning of the apparatus illustrated in FIG. 4 to perform an inspection operation is substantially the same as that of FIG. 3, previously described.

FIG. 5 illustrates a slightly modified embodiment of the invention which is adapted to inspect a pipeline 10" having a diameter larger than the one illustrated in FIG. 4. In this embodiment, core member 30' is a permanent magnet rather than the core of an electromagnet. Furthermore, wire brush pole pieces 35 and 36 are spaced from permanent magnet core 30' by respectively unitary, longitudinally extending spacer members 80 and 81 which are made of a magnetically conductive material.

The elastomeric appendages for supporting transducer housing members 55 and 56 also are somewhat different in FIG. 5. The fin or flap members 46' and 47' are much wider so that they extend beyond the transducer housing members and bend inwardly and are secured to the sides of magnetic core 30'. This type of construction of the flaps 46' and 47' assures that transducer housing members 55 and 56 are maintained in firm but resilient contact with the wall of pipe 10".

The flaps 46' and 47' are secured to longitudinally extending flanges 85 and 86 of spacer member 80 and 81 by means of retainer bars 90 and 91 and bolts, as illustrated. In order that the same flaps 46', 47' and transducer housing members 55 and 56 may be used irrespective of the pipeline diameter, a number of threaded holes may be bored at different vertical positions on the sides of core 30' so that the bolts 94 and 95 may secure the ends of flaps 46' and 47' at different locations on the sides of core 30'. This will permit the flaps to take on different curvatures so that transducer housing members 55 and 56 will contact the walls of different diameter pipes. Alternatively, suitable spacer bars or other adapter means may be employed to change the curvatures of flap members 46' and 47'.

It is to be understood that any or all of the modifications illustrated in FIG. 3 may be incorporated in the apparatus illustrated in FIGS. 1-4, and vice versa.

The embodiments of the invention illustrated in FIGS. 1-5 employ but two pole pieces to couple magnetic flux into the pipeline wall. In the construction of apparatus to inspect a range of very large diameter pipelines, it may be desirable that the basic apparatus be provided with four or more magnetic poles distributed circumferentially around the core, with adjacent poles being of opposite magnetic polarities. With this type of arrangement the lengths of the magnetic circuits may be reduced as compared to the lengths of the circuits if only two pole pieces were used. This alternative arrangement of pole pieces will facilitate the achievement of the desired state of magnetization in the pipe wall.

The inspection apparatus described above provides a number of advantages, both in construction and in use. The fins or flaps 46, 47, and 46', 47' are simple and relatively inexpensive to construct from unitary sheets of elastomeric material. Furthermore, the elastomeric material can withstand considerable shock and abrasion without serious damage and is not subject to corrosion as are metal structures. The flexible nature of the fins permits the transducer housing members to pass over irregularities within the pipeline without damage.

The adaptability of the apparatus to inspect different size pipelines is extremely attractive since one work crew with one basic piece of apparatus may inspect different lines. Other known inspection apparatus of this general type is not readily adaptable and separate apparatus of different size would have to be provided.

I claim:

1. Apparatus for nondestructively inspecting a pipeline by means of inspection apparatus which is propelled through the interior of the pipeline by a fluid which is being transported therethrough, said apparatus comprising means extending longitudinally within a portion of said pipeline and spaced from the wall thereof for establishing a magnetic field directed transversely to the axis of said portion of pipeline, magnetic pole means circumferentially spaced about the wall of the pipeline for directing said magnetic field into the wall of said portion of pipeline to establish a circumferentially directed magnetic flux field therein, a longitudinally extending fin or flap of elastomeric material secured along its longitudinal dimension to said apparatus in the same portion thereof as said means for establishing the magnetic field, said fin extending outwardly with a curved shape toward said wall in a region of the pipeline circumferentially spaced from said magnetic pole means and occupying a circumferential section less than 180°, flux leakage detection means disposed longitudinally along the length of said fin at its outwardly extending portion, said curved fin or flap urging said detection means into firm but resilient contact with the wall of the pipeline, means operable in response to the movement of said apparatus through the pipeline to impart a rotary motion to said apparatus, whereby said detection means follows a helical path along the wall of the pipeline.

2. Inspection apparatus for detecting longitudinally extending anomalies in the wall of a pipeline by nondestructive inspection apparatus which is propelled through the interior of the pipeline by a fluid being transported therethrough, said apparatus comprising a longitudinally extending magnetic core member disposed within said pipeline for establishing a magnetic field directed transversely to the axis of said pipeline, means including longitudinally extending magnetic flux conductive members disposed on opposite sides of said core and adapted to be urged into contact with the wall of the pipe at circumferentially spaced portions thereof for establishing a circumferentially directed magnetic flux field in a longitudinally extending portion of the wall of the pipeline, an elongated unitary sheet of elastomeric material having one longitudinally extending edge secured by fastening means to said core, said sheet extending outwardly in a transverse direction away from said core toward the wall of the pipeline, flaw detecting means disposed longitudinally along the outwardly extended portion of the elastomeric sheet, said elastomeric sheet holding said detecting means in firm but resilient contact with a longitudinally extending portion of the pipeline wall, means responsive to the movement of the inspection apparatus through the pipeline for imparting a helical motion to said core means and flaw detecting means as they move through the pipeline.

3. The combination claimed in claim 2 and further including an electronic equipment housing member attached to said inspection apparatus and adapted to move longitudinally through the pipeline with the inspection apparatus, electronic equipment in the housing member being electrically connected to the detecting means in said inspection apparatus means for causing the housing member to helically rotate with the inspection apparatus, whereby electrical connections between the detecting means in the inspection apparatus and the electronic equipment in the housing member are made without the use of rotary connector means.

4. In apparatus which passes through the interior of a section of pipe to nondestructively detect anomalies in the wall of the pipe, a subcombination of apparatus for resiliently supporting flaw detection means on or adjacent the wall of the pipe comprising an elongated flexible fin-like member secured along its elongated dimension to said inspection apparatus and extending outwardly in the direction toward the wall of the pipe, said member occupying an angular section of the pipe less than 180°, flaw detection means longitudinally disposed along the outwardly extending portion of the member, said member holding the detection means in firm, but yieldable contact with the wall of the pipe.

5. The apparatus claimed in claim 4 wherein said member has a dimension in a direction transverse to the axis of the pipe which is greater than the radial distance between the wall of the pipe and the portion of the apparatus to which the member is secured, said member being curved in a plane transverse to the axis of the pipe in order to fit within the pipe, said detection means being located on the convexly curved side of said member.

6. The apparatus claimed in claim 5 wherein said fin-like member is a unitary sheet of elastomeric material secured along one longitudinal edge portion to the inspection apparatus and the opposite longitudinal edge portion being free, said detection means being disposed adjacent said free edge portion.

7. The apparatus claimed in claim 5 wherein said fin-like member is a unitary sheet of elastomeric material secured along opposite longitudinal edge portions to said inspection apparatus, said detection means being disposed intermediate said edge portions.

8. The apparatus claimed in claim 4 and further including means for changing the radial position of the detection means relative to said apparatus so that said detection means may contact the wall of pipes of different diameters.

9. The apparatus claimed in claim 4 and further including means responsive to longitudinal movement of the apparatus through the pipe for imparting a helical movement to said fin-like member and detection means disposed thereon.

10. Pipeline inspection apparatus for inspecting a section of pipeline from the inside to detect longitudinally extending flaws in the wall of a section of pipe, said apparatus comprising a magnetic core means extending longitudinally within the central portion of said section of pipe for establishing a unidirectional magnetic field directed transversely to the central axis of said pipe, magnetic flux conductive pole pieces disposed on the sides of said core and in flux conductive contact with longitudinally extending and circumferentially spaced portions of the wall of said pipe for establishing a circumferentially directed magnetic flux field in the wall of said pipe, a longitudinally extending sheet of elastomeric material having one edge secured longitudinally along the length of said apparatus to form a fin-like member, said sheet extending outwardly in a transverse direction toward the wall of said pipe, flaw detecting means disposed longitudinally along the outwardly extended portion of said sheet of elastomeric material, said elastomeric sheet holding said detecting means in firm but resilient contact with a longitudinally extending portion of the pipe wall, means responsive to fluid pressure in said pipeline for moving through said section of pipe substantially without rotation and for propelling the apparatus through the pipe, and means carried by said apparatus and responsive to the movement of the apparatus through the pipe for imparting a rotary motion to said core and pole pieces, said elastomeric sheet and said detecting means, whereby said detecting means follows a helical path along the wall of said pipe.

11. The combination claimed in claim 10 and further including an electronic equipment housing member attached to said inspection apparatus and adapted to move longitudinally through the pipeline with the inspection apparatus, electronic equipment in the housing member being electrically connected to the detection means in said inspection apparatus, means for causing the housing member to rotate with the inspection apparatus, whereby electrical connections between the detection means in the inspection apparatus and the electronic equipment in the housing member are made without the use of rotary connector means.

12. Inspection apparatus for detecting longitudinally extending anomalies in the wall of a pipeline by nondestructive inspection apparatus which is propelled through the interior of the pipeline by a fluid being transported therethrough, said apparatus comprising magnetic means comprising a longitudinally extending magnetic core member disposed within said pipeline for establishing a magnetic field directed transversely to the axis of said pipeline, means including longitudinally extending magnetic flux conductive wire brush members disposed on opposite sides of said core, said brush members being in flux conductive contact with the wall of the pipe at circumferentially spaced portions thereof for establishing a circumferentially directed magnetic flux field in a longitudinally extending portion of the wall of the pipeline, an elongated unitary sheet of elastomeric material having one longitudinally extending edge secured by fastening means to said core, said sheet extending outwardly in a transverse direction away from said core toward the wall of the pipeline, flaw detecting means disposed longitudinally along the outwardly extended portion of the elastomeric sheet, said elastomeric sheet holding said detecting means in firm but resilient contact with a longtitudinally extending portion of the pipeline wall, means responsive to the movement of the inspection apparatus through the pipeline for imparting a helical motion to said core means and flaw detecting means as they move through the pipeline, a propelling section responsive to the movement of fluid transported through said pipeline for propelling said apparatus through said pipeline, said propelling section being constructed and arranged to move through the pipeline substantially without rotation, rotary coupling means coupling said propelling section to said core means and said detecting means for permitting relative rotary motion therebetween as said apparatus is propelled through said pipeline, signal recording means rotatable with said detecting means for recording signals produced by said detecting means, and non-rotary electrical connecting means coupling said recording means to said detecting means.

13. The inspection apparatus claimed in claim 12 wherein said wire brush members include respective sole plates from which bristles of the brushes extend transversely thereto, and wherein the means for establishing the circumferentially directed magnetic flux field in the pipeline wall includes longitudinally extending magnetic spacer bars removably secured between, and in contact with, said core and a respective one of said sole plates.

14. The inspection apparatus claimed in claim 12 wherein said fastening means includes means for changing the position of the sheet of elastomeric material relative to said core member to radially move the location of said detecting means relative to said core member.

15. Pipeline inspection apparatus for performing a nondestructive magnetic inspection of said pipeline from the interior of said pipeline to detect longitudinally extending anomalies in the wall of the pipeline, said apparatus comprising a propelling section of the apparatus which includes packer means adapted to make resilient and sliding contact with the wall of said section of pipeline and adapted to be propelled substantially without rotation through a section of the pipeline by a fluid being transported therethrough, means carried by said apparatus for establishing a circumferentially directed magnetic flux field in the wall of a section of said pipeline so that flux lines of said field are directed transversely to longitudinally extending anomalies in said wall, magnetic flux detector means carried on an inspection section of the apparatus for producing inspection signals in response to anomalies detected in a section of pipeline having the circumferentially directed magnetic flux field therein, said detector means comprising one or more longitudinally extending fin-like elastomeric appendages carried by the apparatus and extending transversely toward the wall of the section of pipeline, said one or more appendage each having a circumferential extent not exceeding 180°, flux detector means longitudinally disposed along the transversely extended portion of the appendage, said appendage holding the flux detector means in firm but yieldable inspecting position on or adjacent the wall of said section of pipeline, a plurality of radially extending supporting means circumferentially disposed about and secured to said inspection section, means secured to the opposite end of each of said supporting means for engaging the wall of said pipeline and for imparting a helical motion to the inspection section in response to longitudinal movement of the apparatus relative to the wall of said pipeline, means connecting said propelling section and said inspection section for permitting said inspection section to helically rotate within the section of pipeline as the propelling section moves longitudinally substantially without rotation, inspection signal circuit means included in the apparatus within the pipeline for processing said inspection signals, said circuit means being helically rotatable with said inspection section as the apparatus moves through said pipeline, and nonrotary connector means for electrically connecting said detector means and said circuit means.

16. Apparatus claimed in claim 15 wherein said appendage is comprised of a radially extending sheet of elastomeric material having one longitudinally extending edge secured to said apparatus.

* * * * *